United States Patent
Fayet et al.

(10) Patent No.: US 9,011,822 B2
(45) Date of Patent: Apr. 21, 2015

(54) MIXTURE OF IRON AND COPPER SALTS MASKING METALLIC TASTE

(75) Inventors: Marylène Fayet, Annemasse (FR);
Catherine Kabaradjian,
Vétraz-Monthoux (FR); Patrice Garcin,
saint bonnet prè riom (FR)

(73) Assignee: Bayer Consumer Care AG, Basel (CH)

( * ) Notice: Subject to any disclaimer, the term of this patent is extended or adjusted under 35 U.S.C. 154(b) by 849 days.

(21) Appl. No.: 12/383,647

(22) Filed: Mar. 27, 2009

(65) Prior Publication Data

US 2010/0008865 A1    Jan. 14, 2010

(30) Foreign Application Priority Data

Jan. 4, 2007   (EP) ..................... 07290015

(51) Int. Cl.
| | |
|---|---|
| *A61K 9/12* | (2006.01) |
| *A61K 31/66* | (2006.01) |
| *A61K 9/00* | (2006.01) |
| *A61K 9/46* | (2006.01) |
| *A61K 31/366* | (2006.01) |
| *A61K 33/26* | (2006.01) |
| *A61K 33/34* | (2006.01) |
| *A61K 33/42* | (2006.01) |
| *A61K 9/20* | (2006.01) |

(52) U.S. Cl.
CPC ............ *A61K 9/0056* (2013.01); *A61K 9/0007* (2013.01); *A61K 31/366* (2013.01); *A61K 33/26* (2013.01); *A61K 33/34* (2013.01); *A61K 33/42* (2013.01); *A61K 9/2009* (2013.01)

(58) Field of Classification Search
USPC ..................... 424/647, 43; 514/106
See application file for complete search history.

(56) References Cited

U.S. PATENT DOCUMENTS

| | | | |
|---|---|---|---|
| 5,211,940 A | 5/1993 | Ishiguro et al. | |
| 5,459,162 A | 10/1995 | Saxton | |
| 6,368,621 B1 | 4/2002 | Engel et al. | |
| 6,521,247 B1 | 2/2003 | deVries | |
| 6,779,468 B1 * | 8/2004 | Gupta | 210/647 |
| 7,914,829 B2 * | 3/2011 | Jacquet | 424/729 |
| 2003/0190355 A1 * | 10/2003 | Hermelin et al. | 424/468 |
| 2005/0037065 A1 * | 2/2005 | Kirschner et al. | 424/456 |
| 2005/0170014 A1 | 8/2005 | Krishnan et al. | |

FOREIGN PATENT DOCUMENTS

| | | | |
|---|---|---|---|
| EP | WO 2005/041916 | * | 5/2005 |
| GB | 1322102 | | 7/1973 |
| JP | 01168611 | | 7/1989 |

OTHER PUBLICATIONS

Fu, Yourong, et al., "Orally Fast Disintegrating Tablets: Developments, Technologies, Taste-Masking and Clinical Studies", Critical Reviews in Therapeutic Drug Carrier Systems, 21(6): 433-475 (2004).*
Andrews, N., "Disorders of Iron Metabolism," New England Journal of Medicine, Dec. 23, 1999, 341 (26):1986-1995.
Bhaskaram, P., "Immunobiology of mild micronutrient deficiencies," British Journal of Nutrition, 2001, 85(Supp. 2):S75-S80.
Dallman, P., "Biochemical Basis For The Manifestations Of Iron Deficiency," Annual Rev. Nutr., 1986, 6:13-40.
Haas, et al., "Iron Deficiency and Reduced Work Capacity: A Critical Review of the Research to Determine a Causal Relationship1,2," The Journal of Nutrition, 676S-690S, 2001.

* cited by examiner

*Primary Examiner* — Ernst V Arnold
*Assistant Examiner* — Hong Yu
(74) *Attorney, Agent, or Firm* — Karen B. King

(57) ABSTRACT

A composition comprising iron pyrophosphate and copper citrate does not exhibit the unpleasant taste and aftertaste usually found with iron supplements.

8 Claims, No Drawings

MIXTURE OF IRON AND COPPER SALTS MASKING METALLIC TASTE

This application is a national stage application of PCT Application No. PCT/EP2006/009434, filed on Sep. 28, 2006, which claims priority of PCT Application No. PCT/EP2007/008049, filed Sep. 15, 2007; and European Patent Application No. 07290015.2, filed Jan. 4, 2007.

The present invention relates to an oral composition without metallic taste comprising an iron source which is ferric pyrophosphate and copper citrate as copper source, its process for preparation and its use for balancing the provision of iron as nutritional supplement.

Iron is essential to most life forms and to normal human physiology. Iron is an integral part of many proteins and enzymes that maintain good health. In humans, iron is an essential component of proteins involved in oxygen transport (Dallman, P R, *Biochemical basis for the manifestations of iron deficiency*, Ann Rev Nutr 1986, 6, 13-40). It is also essential for the regulation of cell growth and differentiation (Andrews N C, *Disorders of iron metabolism*, N Eng J Med 1999, 341, 1986-95). A deficiency of iron limits oxygen delivery to cells, resulting in fatigue, poor work performance, and decreased immunity (Haa, J D, Brownlie T 4th. *Iron deficiency and reduced work capacity: a critical review of the research to determine a causal relationship*, J Nutr 2001, 131, 691S-6S,), Bhaskaram P. *Immunobiology of mild micronutrient deficiencies*, Br J Nutr 2001, 85, S75-80).

Several oral compositions are known for the use as nutritional or dietary supplement containing iron. Known compositions are e.g., multi-vitamin and mineral supplements or oral dosage forms containing a higher dose of iron for treating iron deficiency symptoms. However, in order to avoid a bad metallic taste the amount of iron is limited and the use of a complex and expensive taste masking technology such as coating of iron-containing granules or tablets, admixing taste masking flavours, use of capsules is necessary.

The object of the present invention is to provide an alternative oral composition containing an iron source and/or a copper source having no metallic bad taste and avoiding an expensive taste masking technology.

Surprisingly it is found that a metallic bad taste of the composition according to the present invention can be avoided.

Subject of the present invention is an oral composition comprising an iron source which is ferric pyrophosphate and copper citrate as copper source. The oral composition according to the invention has not a metallic bad taste, in particular aftertaste.

According to the present invention ferric pyrophosphate includes any kind of solvate such as hydrates. Preferably the anhydrous form, the monohydrate or the nonahydrate of ferric pyrophosphate is used. Most preferably the nonahydrate of ferric pyrophosphate is used.

According to the present invention copper citrate includes any kind of solvate such as hydrates. Preferably the hemipentahydrate of copper citrate is used.

The amount of the iron source in the composition according to the invention is from 1 to 60 mg, preferably, from 2 to 20 mg based on iron.

The amount of the copper citrate in the composition according to the invention is from 0.1 to 2 mg, preferably 0.3 to 1.1 mg based on copper.

In particular the ratio between iron and copper in the composition is from 1:2 to 50:1, preferably from 5:1 to 25:1, most from 10:1 to 20:1. "Ratio" means for the purposes of the invention the ratio by weight of the individual components based on iron and copper.

The composition according to the invention can comprise further active ingredients such as vitamins and minerals. Vitamins include, but are not limited to, vitamin A, beta carotene, vitamin C (ascorbic acid), vitamin D3 (cholecalcipherol), vitamin E (tocopherol acetate), vitamin B1 (thiamine), vitamin B2 (riboflavin), nicotinamide, vitamin B5 (panthothenic acid), vitamin B6 (pyridoxine), folic acid, vitamin B12 (cyanocobalamin), vitamin K1 and biotin. Minerals include, but are not limited to, calcium salts such as calcium carbonate, calcium phosphate, calcium glycerophosphate; magnesium salts such as magnesium phosphate, magnesium sulphate (dihydrate) or magnesium oxide; zinc salts such as zinc citrate; selenium salts such as sodium selenate; potassium iodide; manganese salts such as manganese sulphate; molybdate salts such as sodium molybdate; chromium salts such as chromium chloride; sodium chloride and potassium chloride.

Subject of the present invention is an oral composition comprising an iron source which is ferric pyrophosphate and copper citrate as copper source and optionally at least one further mineral and/or vitamin.

The composition according to the invention is administered orally one or more, preferably up to three, more preferably up to two times per day. With each administration the number of dosage forms taken in at the same time should not exceed two.

The composition according to the present invention can be used as nutritional supplement or as dietary supplement for balancing the supply of iron in a patient. A patient, for the purpose of this invention, is a mammal, including a human.

Nevertheless, it may in some cases be advantageous to deviate from the amounts specified, depending on body weight, individual behaviour toward the active ingredient, type of preparation and time or interval over which the administration is effected. For instance, less than the aforementioned minimum amounts may be sufficient in some cases, while the upper limit specified has to be exceeded in other cases.

The composition according to the invention comprises suitable administration forms which deliver the compound of the invention and which include, but are not limited to, tablets, tablets which disintegrate rapidly in the oral cavity (orodispersible tablets), powders, sachets, granules, pellets, chewable tablets, chewing gums, dispersible tablets, effervescent compositions such as for example effervescent tablets or effervescent granules, liquids, solutions, emulsions, gels, syrups or drops.

Preference is given to tablets, granules, orodispersible tablets, chewable tablets, chewing gums, dispersible tablets, effervescent tablets and effervescent granules. More preferably the application forms are chewable tablets, orodispersible tablets, chewing gums, dispersible tablets, effervescent tablets and effervescent granules.

Ingredients of the oral dosage forms are those which are accepted for pharmaceuticals and nutritional supplements and physiologically unobjectionable, for example: as fillers cellulose derivatives (e.g. microcrystalline cellulose), sugars (e.g. lactose), sugar alcohols (e.g. mannitol, sorbitol), inorganic fillers (e.g. calcium phosphates), binders (e.g. polyvinylpyrrolidone, gelatin, starch derivatives and cellulose derivatives), and all other excipients required to produce formulations of pharmaceuticals and nutritional supplements of the desired properties, e.g. lubricants (magnesium stearate), e.g. disintegrants (e.g. crosslinked polyvinylpyrrolidone, sodium carboxymethylcellulose), e.g. wetting agents (e.g.

sodium lauryl sulphate), e.g. release slowing agents (e.g. cellulose derivatives, polyacrylic acid derivatives), e.g. stabilizers, e.g. sweeteners, e.g. antioxidants, e.g. preservatives, e.g. flavourings, e.g. coloured pigments, e.g. effervescent couples preferably citric acid as acid component and sodium carbonate and/or sodium hydrogen carbonate as basic component.

Liquid formulations are likewise produced by a standard method using excipients which are usual for pharmaceuticals and nutritional supplements and contain the active ingredients either dissolved or suspended. Typical administration volumes of these pharmaceutical and nutritional supplement preparations are 1 to 10 ml. Examples of excipients in these liquid formulations are: solvents (e.g. water, alcohol, and natural and synthetic oils, e.g. medium chain-link triglycerides), solubilizers (e.g. glycerol, glycol derivatives), wetting agents (e.g. polysorbate, sodium lauryl sulphate), and further excipients required to produce formulations of pharmaceuticals and nutritional supplements of the desired properties, e.g. viscosity-increasing agents, e.g. pH-correcting agents, e.g. sweeteners and flavourings, e.g. antioxidants, e.g. stabilizers, e.g. preservatives.

Excipients for pharmaceuticals and nutritional supplements familiar to the skilled person are also described for example in the following handbook: "Handbook of Pharmaceutical Excipients," Rowe R. C., Sheskey P. J. & Weller, P. J., American Pharmaceutical Association, Washington, 4th edition 2003.

The dosage forms mentioned herein are produced by standard processes. E.g. Tablets or chewable tablets can be produced by mixing and/or granulating the active ingredients together with the excipients to form a blend which is finally pressed to tablets. Optionally different blends containing different ingredients and excipients can be premixed and combined to a final blend which is then pressed to tablets. In the case of an effervescent formulation the acid/base couple can be add e.g. to final blend or the acid and the base are added at different times to the blend. Also the base and the acid can be added to different blends which are finally combined.

Advantage of the composition of the present invention is that for the preparation of the composition a complex and expensive taste masking technology known in the prior art such as coating of tablets or coating of granules or putting the iron component into a capsule is not needed. The composition of the present invention can be prepared by simple and well-known standard procedures. Another well-known taste masking method is the addition of flavours in order to cover and mask the bad taste. This taste masking method is normally restricted to only a few applicable flavours which have to be selected in each case. However, flavouring ingredients are not needed for taste masking in the composition of the present invention.

Subject of the present invention is an oral composition comprising an iron source which is ferric pyrophosphate and copper citrate as copper source which has no metallic taste in particular after taste and which is not a coated tablet, coated granule or capsule.

Subject of the present invention is an oral composition comprising an iron source which is ferric pyrophosphate and copper citrate as copper source and optionally at least one further mineral and/or vitamin wherein the composition has no metallic taste and is not a coated tablet, coated granule or capsule.

Preference is given to a fast disintegrating orodispersible tablet, a chewable tablet or an effervescent formulation. The disintegration time of the disintegrating orodispersible tablet is less equal than 100 sec., preferably less equal than 80 sec.

EXAMPLES

Example 1

| Orodispersible tablet Active Ingredients | Amount based on the active ingredient [mg] | Tablet weight 1000 mg Form of the active ingredient | Amount of the form of the active ingredient [mg] |
|---|---|---|---|
| vit A | 400 | vitamin A palmitate 100000 IU/g | 13.33 |
| vit C | 30 | ascorbic acid | 30 |
| Vit D3 | 2,5 | cholecalciferol 100000 IU/g | 0.8 |
| vit E | 5 | tocopherol acetate 50% CWS/F | 14 |
| thiamin (B1) | 1,05 | thiamin nitrate 33% Rocoat | 3.9 |
| riboflavin (B2) | 1,2 | riboflavine 33% Rocoat | 3.6 |
| nicotinamide (PP) | 13,5 | nicotinamide | 13.5 |
| pantothenic acid (B5) | 3 | calcium pantothenate | 3.26 |
| pyridoxine (B6) | 1,5 | pyridoxine hydrochloride 33% Rocoat | 5.46 |
| folic acid | 150 | folic acid 10% trituration | 1.5 |
| Cyanocobalamin (B12) | 0,75 | dry vit B12 0,1% WS | 0.75 |
| biotin | 75 | biotin 1% trituration | 7.5 |
| calcium | 60 | calcium carbonate DCCS90L | 166.53 |
| magnesium | 25 | magnesium oxide | 41.45 |
| iron | 4 | Ferric pyrophosphate | 16.0 |
| zinc | 3,75 | Zinc citrate trihydrate | 12.02 |
| iodine | 37,5 | potassium iodide 5% trituration | 0.75 |
| selenium | 25 | sodium selenate anhydrous 1% trituration | 2.5 |
| copper | 0,45 | copper citrate 2.5 $H_2O$ | 1.28 |
| manganese | 0,9 | manganese sulfate monohydrate | 2.77 |
| molybdenum | 22,5 | sodium molybdate dihydrate 1% trituration | 2.25 |
| chromium | 12,5 | chromic chloride hexahydrate 1% trituration | 1.25 |
| Pharmaburst C1 | | | qs 1 tablet |
| anhydrous citric acid | | | 16 |
| magnesium stearate | | | 25 |

-continued

| Orodispersible tablet Active Ingredients | Amount based on the active ingredient [mg] | Tablet weight 1000 mg Form of the active ingredient | Amount of the form of the active ingredient [mg] |
|---|---|---|---|
| sodium hydrogencarbonate | | | 20 |
| pineapple flavour | | | 3 |
| passion fruit flavour | | | 3 |
| aspartame | | | 13 |
| iron oxide | | | 2.5 |

Pharmaburst C1 is commercially available (SPI Pharma, US Drug Masterfile Number:17044; U.S. Pat. No. 7,118,765).

Example 2

| Orodispersible tablet Active ingredients | Amount based on the active ingredient [mg] | Tablet weight 1000 mg Form of the active ingredient | Amount of the form of the active ingredient [mg] |
|---|---|---|---|
| vit A | 400 | vitamin A palmitate 100000 IU/g | 13.33 |
| vit C | 30 | ascorbic acid | 30 |
| Vit D3 | 2,5 | cholecalciferol 100000 IU/g | 0.8 |
| vit E | 5 | tocopherol acetate 50% CWS/F | 14 |
| thiamin (B1) | 1,05 | thiamin nitrate 33% Rocoat | 3.9 |
| riboflavin (B2) | 1,2 | riboflavine 33% Rocoat | 3.6 |
| nicotinamide (PP) | 13,5 | nicotinamide | 13.5 |
| pantothenic acid (B5) | 3 | calcium pantothenate | 3.26 |
| pyridoxine (B6) | 1,5 | pyridoxine hydrochloride 33% Rocoat | 5.46 |
| folic acid | 150 | folic acid 10% trituration | 1.5 |
| Cyanocobalamin (B12) | 0,75 | dry vit B12 0.1% WS | 0.75 |
| biotin | 75 | biotin 1% trituration | 7.5 |
| calcium | 60 | calcium carbonate DCCS9OL | 166.53 |
| magnesium | 25 | magnesium oxide | 41.45 |
| iron | 4 | ferric pyrophosphate | 16.0 |
| zinc | 3,75 | Zinc citrate trihydrate | 12.02 |
| iodine | 37,5 | potassium iodide 5% trituration | 0.75 |
| selenium | 25 | sodium selenate anhydrous 1% trituration | 2.5 |
| copper | 0,45 | Copper citrate 2.5 H$_2$O | 1.28 |
| manganese | 0,9 | manganese sulfate monohydrate | 2.77 |
| molybdenum | 22,5 | sodium molybdate dihydrate 1% trituration | 2.25 |
| chromium | 12,5 | chromic chloride hexahydrate 1% trituration | 1.25 |
| F-melt grade C | | | qs 1 tablet |
| anhydrous citric acid | | | 16 |
| magnesium stearate | | | 25 |
| sodium hydrogencarbonate | | | 20 |
| pineapple flavour | | | 3 |
| Passion fruit flavour | | | 3 |
| aspartame | | | 13 |
| iron oxide | | | 2.5 |

F-Melt grade C is commercially available (Fuji Chemical Industry Co., Ltd., Japan) and contains D-mannitol, xylitol, microcrystalline cellulose, crospovidone and dibasic calcium phosphate.

Manufacturing Process for Orodispersible Tablets

Premix:

In a drum dry vitamin D3, thiamine mononitrate, riboflavin, pyridoxine hydrochloride, folic acid, vitamin B 12, calcium pantothenate, biotin, copper citrate 2,5 H$_2$O, manganese sulphate monohydrate, iodine, selenium, chromium, molybdenum, pineapple flavour, passion fruit flavour, iron oxide yellow, aspartame and a part of the disintegrant (e.g. Pharmaburst C1, F-Melt grade C) are mixed for 15 minutes.

Final Blend:

Premix, vitamin A palmitate, nicotinamide, dry vitamin E, ascorbic acid, calcium carbonate, magnesium oxide heavy, iron source, zinc citrate 3 H$_2$O, anhydrous citric acid, sodium hydrogen carbonate and the rest of the pharmaburst C1 or F-melt are mixed for 20 minutes. Thereafter magnesium stearate is added and is mixed again for 5 additional minutes.

Compression:

The homogeneous final blend is compress to tablets on a rotary tablet press.

Example 3

| Effervescent tablet Active ingredients | Amount based on the active ingredient | Tablet weight 4800 mg Form of the active ingredient | Amount of the form of the active ingredient |
|---|---|---|---|
| vit A as retinol | (2667.7 IU) 800 µg | vitamin A palmitate 100000 IU/g | (2266.7 IU) 22.67 mg |
|  |  | beta carotene as betatab 10%E | (400 IU) 7.20 mg |
| vitamin D3 | (200 IU) 5 µg | Cholecalciferol concentrate (water dispersible powder form) 100000 IU/g | 2.0 mg |
| Vitamin E | 10 mg | D-alpha-tocopherol acetate concentrate (powder form) 50% | 29.80 mg |
| Vitamin K | 0.03 mg | vitamin K1 5% SD | 0.60 mg |
| Vitamin B1 | 4.20 mg | Thiamin monophosphoric acid ester chloride dehydrate | 6.59 mg |
| Vitamin B2 | 4.80 mg | Sodium riboflavin 5'-phosphate | 6.56 mg |
| Niacin | 54.0 mg | nicotinamide | 54.0 mg |
| Pantothenic acid | 18.0 mg | Calcium D-pantothenate | 19.57 mg |
| Vitamin B6 | 6.0 mg | Pyridoxine hydrochloride | 7.3 mg |
| Folic acid | 0.60 mg | Pteroylmonoglutamic acid | 0.60 mg |
| Vitamin B12 | 3.0 µg | Cyanocobalamin powder 0.1% water soluble | 3.0 mg |
| Biotin | 30 µg | D-biotin | 30 µg |
| Vitamin C | 180 mg | Ascorbic acid fine powder | 180 mg |
| Calcium | 120 mg | Calcium carbonate (see calcium pantothenate) | 295.61 mg |
| Magnesium | 80 mg | Magnesium carbonate | 163 mg |
|  |  | Magnesium sulphate dihydrate | 257.4 mg |
| Iron | 14 mg | Ferric pyrophosphate | 56 mg |
| copper | 0.9 mg | Copper citrate 2.5 hydrate | 2.57 mg |
| iodine | 0.075 mg | Potassium iodine | 0.098 mg |
| zinc | 8 mg | Zinc citrate trihydrate | 25.63 mg |
| manganese | 1.8 mg | Manganese sulphate monohydrate | 5.54 mg |
| potassium | 20.4 mg | Potassium chloride | 38.96 mg |
| selenium | 50 µg | Sodium selenate anhydrous | 0.12 mg |
| chromium | 0.025 mg | Chromium chloride hexahydrate | 0.128 mg |
| molybdenum | 0.045 mg | Sodium molybdate dihydrate | 0.113 mg |
| Coenzyme Q10 | 3.0 mg | Coenzyme Q10 10 % | 30 mg |

Further excipients can be added to example 3:

| excipients | Amount [mg] |
|---|---|
| Mannitol 100 mesh [2)] | qs |
| Mannitol SD 200 [1)] | qs |
| Sorbitol [1)] | qs |
| Anhydrous citric acid | 1,800 |
| Sodium hydrogen carbonate | 950 |
| Orange juice flavour | 77 |
| Sodium carbonate | 65 |
| Passion fruit flavour | 30 |
| aspartame | 35 |
| Potassium acesulfam | 20 |
| crospovidone | 7 |
| beet red juice powder | 5 |
| sucrose ester of fatty acids | 0.15 | qs: quantum satis = quantity to add to reach the tablet weight
[1)] Half of mannitol SD 200 and half of sorbitol are used to obtain the theoretical tablet weight of 4800 mg.
[2)] The quantity of mannitol 100 mesh is adjusted according to mineral contents in the granule.

Example 4

| Effervescent tablet Active ingredients | Tablet weight 4400 mg Form of the active ingredient | Amount |
|---|---|---|
| Vitamin A | vitamin A 100 WS | 28.929 mg |
| vitamin D3 | Vitamin D3 100 SD/S | 3.6 mg |
| Vitamin E | Vitamin E 50 % CWS/S | 98.34 mg |
| Vitamin B6 | Vitamin B6 HCl | 8.701 mg |
| Vitamin C | Vitamin C | 207.9 mg |
| Vitamin B12 | Vitamin B12 0.1% WS | 3.9 mg |
| Folic acid | Folic acid | 0.5 mg |
| Zinc citrate | Zinc citrate | 32.04 mg |
| iron | Ferreous pyrophosphate | 21 mg |
| copper | Copper citrate 2.5 hydrate | 2.678 mg |
| Selen | Selen trituration 1% | 10.5 mg |
| Citric acid | Citric acid | 1500 mg |
| Sodium hydrogencarbonate | Sodium hydrogencarbonate | 1000 mg |
| Sodium carbonate | Sodium carbonate | 65 mg |
| isomalt | Isomalt DC100 | 1208.912 mg |
| aspartame | aspartame | 40 mg |
| acesulfame | Potassium acesulfame | 20 mg |
| betacaroten | Betacaroten 1% CWS | 10 mg |
| Red beet | Red beet | 13 mg |
| riboflavine | Riboflavine phosphate | 10 mg |
| Orange flavor | Orangeultraseal | 105 mg |
| tangerine | tangerine | 10 mg |

Example 4 is manufactured corresponding to example 3.

Manufacturing Process for Example 3:

Vitamin Blend:

In a drum vitamin D3 100 CWS, biotin, folic acid, vitamin B12 0.1% WS, vitamin K1 5% SD, coenzyme Q10 10% CWS/S, sodium molybdate dihydrate, sodium selenate anhydrous and mannitol (a part) are mixed together to the premix 1. Into the tank of the blender the following ingredients are introduced and mixed: premix 1, vitamin A palmitate, nicotinamide, calcium pantothenate, vitamin E powder, pyridoxine hydrochloride, riboflavin sodium phosphate, thiamin monophosphoric, betatab 10% E, crospovidone, beet red juice powder and mannitol (a part).

Mineral Granule:

The following ingredients are mixed: copper citrate 2.5 $H_2O$, zinc citrate trihydrate, iron source, manganese sulfate monohydrate, calcium carbonate, magnesium carbonate, magnesium sulfate dihydrate, sodium hydrogen carbonate, potassium chloride, anhydrous citric acid and mannitol (rest). Thereafter the mixture is granulated by spraying a binding solution made of ethanol, sucrose esters of fatty acids, potassium iodide and chromium chloride hexahydrate. The granule is dried, cooled and sieved.

Final Blend:

In the tank of the tumble mixer the mineral granule, the vitamin blend, ascorbic acid, sodium hydrogen carbonate, sorbitol, anhydrous sodium carbonate, sodium chloride, orange flavour, passion fruit flavour, potassium acesulfame, aspartame and mannitol SD 200 are mixed to the final blend.

Tabletting:

The homogeneous final blend is compressed to tablets on a rotary tablet press.

Results:

Examples 1 and 3 do not show a metallic bad taste when administered orally.

The disintegration time for example 1 (orodispersible tablets) is 67 sec.

What is claimed is:

1. An oral nutritional supplement comprising ferric pyrophosphate and copper citrate, wherein the nutritional supplement is in the form of an effervescent composition.

2. The oral nutritional supplement of claim 1, wherein the effervescent composition is a tablet or effervescent granules.

3. The oral nutritional supplement of claim 1, comprising from about 0.1 to about 2 mg of copper.

4. The oral nutritional supplement of claim 1, comprising from about 0.3 to about 1.1 mg of copper.

5. The oral nutritional supplement of claim 1, comprising from about 1 to about 60 mg iron.

6. The oral nutritional supplement of claim 1, further comprising at least one additional ingredient selected from the group consisting of minerals and vitamins.

7. The oral nutritional supplement of claim 1, in the form of an effervescent tablet of about 4800 mg comprising the following composition of active ingredients:

| Active ingredients | Amount based on the active ingredient |
|---|---|
| vit A as retinol | (2667.7 IU) |
| | 800 µg |
| vitamin D 3 | (200 IU) |
| | 5 µg |
| Vitamin E | 10 mg |
| Vitamin K | 0.03 mg |
| Vitamin B1 | 4.20 mg |
| Vitamin B2 | 4.80 mg |
| Niacin | 54.0 mg |
| Pantothenic acid | 18.0 mg |
| Vitamin B6 | 6.0 mg |
| Folic acid | 0.60 mg |
| Vitamin B12 | 3.0 µg |
| Biotin | 30 µg |
| Vitamin C | 180 mg |
| Calcium | 120 mg |
| Magnesium | 80 mg |
| Iron | 14 mg |
| copper | 0.9 mg |
| iodine | 0.075 mg |
| zinc | 8 mg |
| manganese | 1.8 mg |
| potassium | 20.4 mg |
| selenium | 50 µg |
| chromium | 0.025 mg |
| molybdenum | 0.045 mg |
| Coenzyme Q10 | 3.0 mg | and at least one excipient.

8. The nutritional supplement of claim 7, wherein the active ingredients are present in the following form and amount:

| Form of the active ingredient | Amount of the form of the active ingredient |
|---|---|
| vitamin A palmitate 100000 IU/g | (2266.7 IU) |
| | 22.67 mg |
| beta carotene as betatab 10% E | (400 IU) |
| | 7.20 mg |
| Cholecalciferol concentrate (water dispersible powder form) 100000 IU/g | 2.0 mg |
| D-alpha-tocopherol acetate concentrate (powder form) 50% | 29.80 mg |
| vitamin K1 5% SD | 0.60 mg |
| Thiamin monophosphoric acid ester chloride dihydrate | 6.59 mg |
| Sodium riboflavin 5'-phosphate | 6.56 mg |
| nicotinamide | 54.0 mg |
| Calcium D-pantothenate | 19.57 mg |
| Pyridoxine hydrochloride | 7.3 mg |
| Pteroylmonoglutamic acid | 0.60 mg |
| Cyanocobalamin powder 0.1% water soluble | 3.0 mg |
| D-biotin | 30 µg |
| Ascorbic acid fine powder | 180 mg |
| Calcium carbonate | 295.61 mg |
| Magnesium carbonate | 163 mg |
| Magnesium sulphate dihydrate | 159 mg |
| Ferric pyrophosphate | 56 mg |
| Copper citrate 2.5 hydrate | 2.57 mg |
| Potassium iodine | 0.098 mg |
| Zinc citrate trihydrate | 25.63 mg |
| Manganese sulphate monohydrate | 5.54 mg |
| Potassium chloride | 38.96 mg |
| Sodium selenate anhydrous | 0.12 mg |
| Chromium chloride hexahydrate | 0.128 mg |
| Sodium molybdate dihydrate | 0.113 mg |
| Coenzyme Q10 10% | 30 mg | and at least one excipient.

* * * * *